(12) United States Patent
Jahns et al.

(10) Patent No.: US 6,960,205 B2
(45) Date of Patent: *Nov. 1, 2005

(54) SUCTION STABILIZED EPICARDIAL ABLATION DEVICES

(75) Inventors: Scott E. Jahns, Hudson, WI (US); Donald N Jensen, Roseville, MN (US); David Lipson, North Andover, MA (US); Jon M. Ocel, New Brighton, MN (US); Gregory P. Werness, South St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 113 days.

This patent is subject to a terminal disclaimer.

(21) Appl. No.: 10/292,117

(22) Filed: Nov. 12, 2002

(65) Prior Publication Data

US 2003/0078575 A1 Apr. 24, 2003

Related U.S. Application Data

(63) Continuation of application No. 09/558,976, filed on Apr. 27, 2000, now Pat. No. 6,514,250.

(51) Int. Cl.⁷ .............................................. A61B 18/18
(52) U.S. Cl. ............................ 606/41; 606/48; 607/102
(58) Field of Search ...................... 606/41, 42, 45–50; 607/101, 102, 119, 122, 126–128; 601/6, 7; 600/387

(56) References Cited

U.S. PATENT DOCUMENTS

| | | | |
|---|---|---|---|
| 5,336,252 A | * | 8/1994 | Cohen .......................... 607/119 |
| 5,405,376 A | | 4/1995 | Mulier et al. |
| 5,452,733 A | | 9/1995 | Sterman et al. |
| 5,487,757 A | | 1/1996 | Truckai et al. |
| 5,540,681 A | | 7/1996 | Strul et al. |
| 5,545,200 A | | 8/1996 | West et al. |
| 5,571,088 A | | 11/1996 | Lennox et al. |
| 5,571,215 A | | 11/1996 | Sterman et al. |
| 5,573,533 A | | 11/1996 | Strul |
| 5,588,432 A | | 12/1996 | Crowley |
| 5,643,197 A | * | 7/1997 | Brucker et al. ............... 604/20 |
| 5,725,524 A | | 3/1998 | Mulier et al. |
| 5,755,760 A | | 5/1998 | Maguire et al. |
| 5,779,699 A | | 7/1998 | Lipson |
| 5,797,960 A | | 8/1998 | Stevens et al. |
| 5,807,395 A | | 9/1998 | Mulier et al. |
| 5,823,955 A | | 10/1998 | Kuck et al. |
| 5,836,311 A | * | 11/1998 | Borst et al. .................. 128/897 |
| 5,840,031 A | | 11/1998 | Crowley |

(Continued)

FOREIGN PATENT DOCUMENTS

| WO | WO 01/05306 | 1/2001 |
|---|---|---|
| WO | WO 01/58373 | 8/2001 |

OTHER PUBLICATIONS

An article entitled "Radiofrequency Ablation of Cardiac Arrhytmias" (Lawrence S. Klein and William M. Miles, Scientific American Science & Medicine May/Jun. 1994, pp. 48–57.

(Continued)

*Primary Examiner*—Michael Peffley
(74) *Attorney, Agent, or Firm*—Tom Berry; Jeffrey J. Hohenshell

(57) ABSTRACT

A suction assisted ablation device having a support surface, suction elements disposed adjacent the support surface, at least one electrode and at least one suction conduit is provided. The device may further include fluid openings, which allow fluid to irrigate target tissue and aid in ablation. A method for ablating tissue using suction is also provided.

28 Claims, 5 Drawing Sheets

U.S. PATENT DOCUMENTS

| | | | |
|---|---|---|---|
| 5,876,398 | A | 3/1999 | Mulier et al. |
| 5,913,854 | A | 6/1999 | Maguire et al. |
| 5,916,213 | A | 6/1999 | Haissaguerre et al. |
| 5,916,214 | A | 6/1999 | Cosio et al. |
| 5,919,188 | A | 7/1999 | Shearon et al. |
| 5,931,810 | A | 8/1999 | Grabek |
| 5,971,983 | A * | 10/1999 | Lesh .......................... 606/41 |
| 6,002,955 | A | 12/1999 | Willems et al. |
| 6,004,269 | A | 12/1999 | Crowley et al. |
| 6,016,809 | A | 1/2000 | Mulier et al. |
| 6,019,722 | A | 2/2000 | Spence et al. |
| 6,051,008 | A | 4/2000 | Saadat et al. |
| 6,063,081 | A | 5/2000 | Mulier et al. |
| 6,068,629 | A | 5/2000 | Haissaguerre et al. |
| 6,086,583 | A | 7/2000 | Ouchi |
| 6,159,207 | A | 12/2000 | Yoon |
| 6,159,208 | A | 12/2000 | Hovda et al. |
| 6,161,543 | A | 12/2000 | Cox et al. |
| 6,162,195 | A | 12/2000 | Igo et al. |
| 6,165,174 | A | 12/2000 | Jacobs et al. |
| 6,183,469 | B1 | 2/2001 | Thapliyal et al. |
| 6,190,353 | B1 | 2/2001 | Makower et al. |
| 6,190,381 | B1 | 2/2001 | Olsen et al. |
| 6,231,518 | B1 | 5/2001 | Grabek et al. |
| 6,237,605 | B1 | 5/2001 | Vaska et al. |
| 6,258,087 | B1 * | 7/2001 | Edwards et al. ............... 606/41 |
| 6,311,692 | B1 * | 11/2001 | Vaska et al. ................. 128/898 |
| 6,425,912 | B1 | 7/2002 | Knowlton |
| 6,514,249 | B1 | 2/2003 | Maguire et al. |
| 6,652,518 | B2 * | 11/2003 | Pendekanti et al. ........... 606/41 |
| 6,663,622 | B1 * | 12/2003 | Foley et al. ................... 606/34 |

OTHER PUBLICATIONS

An article entitled"Physiology of the Heart" Conduction System (A, Unit Four Transportation, pp. 472–479??).

An article entitled "Transcatheter Radiofrequency Ablation of Atrial Tissue Using a Suction Catheter" (Th Lavergne, L. Pruner, L. Cuinze, P. Bruneval, *D. Von Euw, J–Y. Le Heuzy and P. Peronneau, (From the Inserm U 256 & 28 (*), Paris, France.) PACE, vol. 12, Jan. 1989, Part II, pp. 177–186).

An article entitled "Radiofrequency Ablation of Atrial Fibrillation in Patients undergoing concornitant Cardiac Surgery. First Experience" (Willem P. Beukema, MD, Hauw T. Sie, MD, Anand R. Ramdat Misier, MD, Max Haalebos, MD, Cor. W. Schipper, Hospital De Weezenlanden, Zwolle, The Netherlands; PACE Apr. 1997; 20 (Part II), P. 1100 (abstract only).

An article entitled "Efficacy of a Simple Left Atrial Procedure for Chronic Atrial Fibrillation in Mitral Valve Operations," (Taihiro Suda, MD, et al., Haidyuki Nagata, MD, Kazumasa Orihashi, MD, Satoru Moria, MD, Kenji Okada, MD, Masafumi Sueshiro, MD, Shinji Hirai, MD, and Yuichiro Matsuura, MD, First Department of Surgery, Hiroshima University, School of Medicine, Hiroshima, Japan, © 1997 by the Society of Thoracic Surgeons, pp. 1070–1075; Ann Thoracic Surg 1997; 63:1075).

An article entitled "Minimally Invasive Endocardial and Epicardial Maze Procedure" ( The Pennsylvania State University, Milton S. Hershey Medical Center, Hershey, Pennsylvania, Revised: Nov. 25, 1998, pp. 1–25).

Abstracts From the $70^{th}$ Scientific Session entitled "Early Results of Cox–Maze Procedure Combined with Miral Valve Repair"(Nobuhiro Handa, Hartzell V. Schaff, Betty J. Anderson, Stephen L. Kopecky, Mayo Clinic, Rochester, MN Circulation, 1997; 96 (8, Suppl): p. 1–731 (abstract only).

Grundeman, P.F., Experimental videothoracoscopic cannulation of the left atrial appendix: a feasible rapid approach for initiating left heart bypass? 1993, vol. 7; No. 6, Pagination 511, Journal—*Surgical Endoscopy*.

Thomas, Stuart P. et al., Mechanism, Localization and Cure of Atrial Arrhythmias Occurring After A New Intraoperative Endocardial Radiofrequency Ablation Procedure for Atrial Fibrillation, Nov. 2, 2000, vol. 35, *Journal of the American College of Cardiology*.

* cited by examiner

SUCTION STABILIZED EPICARDIAL ABLATION DEVICES

This patent application is a continuation of U.S. patent application Ser. No. 09/558,976, filed Apr. 27, 2000, now U.S. Pat. No. 6,514,250, the entire contents of which is specifically incorporated herein by reference.

FIELD OF THE INVENTION

This invention relates to ablation devices that are used to create lesions in tissue. More particularly, this invention relates to ablation devices that use vacuum or suction force to hold the tissue in a manner that creates linear lesions.

BACKGROUND OF THE INVENTION

The action of the heart is known to depend on electrical signals within the heart tissue. Occasionally, these electrical signals do not function properly. Ablation of cardiac conduction pathways in the region of tissue where the signals are malfunctioning has been found to eliminate such faulty signals. Ablation is also used therapeutically with other organ tissue, such as the liver, prostate and uterus. Ablation may also be used in treatment of disorders such as tumors, cancers or undesirable growth.

Currently, electrophysiology (EP) ablation devices generally have one or more electrodes at their tips. These devices may be used for both diagnosis and therapy. In one instance, electrodes at the tips of EP ablation devices allow the physician to measure electrical signals along the surface of the heart. This is called mapping. When necessary, in another instance, the physician can also ablate certain tissues using, typically, radio frequency (RF) energy conducted to one or more ablation electrodes.

Sometimes ablation is necessary only at discrete positions along the tissue, is the case, for example, when ablating accessory pathways, such as in Wolff-Parkinson-White syndrome or AV nodal reentrant tachycardias. At other times, however, ablation is desired along a line, called linear ablation. This is the case for atrial fibrillation, where the aim is to reduce the total mass of electrically connected atrial tissue below a threshold believed to be critical for sustaining multiple reentry wavelets. Linear lesions are created between electrically non-conductive anatomic landmarks to reduce the contiguous atrial mass.

Linear ablation is currently accomplished in one of several ways. One way is to position the tip portion of the ablation device so that an ablation electrode is located at one end of the target site. Then energy is applied to the electrode to ablate the tissue adjacent to the electrode. The tip portion of the electrode is then slid along the tissue to a new position and then the ablation process is repeated. This is sometimes referred to as the burn-drag-burn technique. This technique is time-consuming (which is not good for the patient) and requires multiple accurate placements of the electrode (which may be difficult for the physician). Furthermore, even if the ablation process creates a continuously linear line along the top surface of the target tissue, it is not assured that the tissue is continuously and completely ablated through further layers of the target tissue (i.e. it is not assured that transmurality is achieved.)

A second way of accomplishing linear ablation is to use an ablation device having a series of spaced-apart band or coil electrodes which, after the electrode portion of the ablation device has been properly positioned, are energized simultaneously or one at a time to create the desired lesion. If the electrodes are close enough together the lesions run together sufficiently to create a continuous linear lesion. While this technique eliminates some of the problems associated with the burn-drag-burn technique, some repositioning of the ablation device may be required to create an adequately long lesion. In addition, it may be difficult to obtain adequate tissue contact pressure for each electrode in a multi-electrode ablation device. Also, the use of multiple electrodes to create the linear lesion tends to make the tip portion more expensive to make, more bulky and may cause the tip portion to be stiffer than with a single electrodes.

Another ablation-related problem results from the delivery of RF energy to muscular tissue, such as the heart. Ablation of such tissue using conventional ablation devices has a tendency to char or burn the blood or tissue with which the electrodes are in contact if the temperatures exceed a certain threshold (for example, greater than 50° C.). This increases the difficulty of the ablation process because it is necessary to clean the tip portion after a series of burns. Moreover, overheating the blood in the vicinity of the target site can desiccate the blood and can cause overburning.

It would be desirable to have an ablation device which is easy to position in relation to the target tissue and which stays stable in position in relation to the target tissue.

It would further be desirable to have an ablation device which, when positioned, is capable of easily creating a linear, transmural lesion.

It would further be desirable to have an ablation device that is able to monitor tissue temperature in order to avoid burning the tissue.

SUMMARY OF THE INVENTION

One aspect of the present invention provides a suction assisted ablation device. The device includes a support surface, having a first and a second face, a plurality of suction elements disposed adjacent the support surface on the first face, at least one conductive element disposed adjacent the support surface on the first face, and at least one suction conduit operatively connected with the suction elements. The device may also include a maneuvering apparatus, such as a pull wire assembly. The device may also include at least one thermocouple element. The device may include one conductive element on a first support surface and a separate conductive element on a second support surface. The conductive element may be a plurality of needle electrodes. The device may also include at least one fluid opening, which may be located within the conductive element. The conductive element may also be made of a material capable of releasing fluid.

Another aspect of the invention provides a method of ablating tissue. A suction assisted ablation device comprising a support surface, having a first and a second face, a plurality of suction elements disposed adjacent the support surface on the first face, and at least one conductive element disposed adjacent the support surface on the first face is provided. The first face of the device is placed adjacent an area of tissue. Suction is conducted to the suction elements via the suction conduit. The tissue is grasped with the suction and ablated. At least one fluid outlet may be provided adjacent the support surface and fluid may be released via the fluid outlet. The fluid outlet may be located within the conductive element. The device may be placed using a maneuvering apparatus. At least one thermocouple element may be placed in communication with at least one suction element and a thermal environment of the suction element may be measured using the thermocouple element. The tissue may be ablated until the measurement of the thermal environment reaches a given level. A second support surface having a second conductive element disposed adjacent a first face of the second support surface may also be provided. The first face of the second support surface may be placed in line with the first support surface to complete a circuit. The tissue is ablated.

Another aspect of the invention provides a tissue ablation system. The system comprises at least two support surfaces, each support surface having a first and a second face, a plurality of suction elements disposed adjacent the support surface on the first face, at least one conductive element disposed adjacent the support surface on the first face, at least one suction conduit operatively connected with the suction elements, and at least one maneuvering apparatus, such as a pull wire assembly. The support surfaces may be disposed consecutively to each other in a linear manner along the maneuvering apparatus so that a continuous ablation lesion is achieved. The system may also include a fluid delivery system, which may incorporate at least one fluid opening disposed adjacent the support surface, a fluid conduit, a conductive element including fluid openings or a conductive element made of a material that releases fluid.

Another aspect of the invention provides a method of mapping the heart. A suction assisted ablation device comprising a support surface, having a first and a second face, a plurality of suction elements disposed adjacent the support surface on the first face, at least one electrode disposed adjacent the support surface on the first face and at least one suction conduit operatively connected with the suction elements is provided. The first face of the device is placed adjacent an area of tissue. Suction is conducted to the suction elements via the suction conduit. The tissue is grasped with the suction. A signal is sent through a first electrode. The signal is received through a second electrode. The distance is mapped based on the signal from the first electrode to the second electrode.

Another aspect of the invention provides a method of pacing a heart. A suction assisted ablation device comprising a support surface, having a first and a second face, a plurality of suction elements disposed adjacent the support surface on the first face, at least one electrode disposed adjacent the support surface on the first face and at least one suction conduit operatively connected with the suction elements. The first face of the device is placed adjacent an area of tissue. Suction is conducted to the suction elements via the suction conduit. The tissue is grasped with the suction. Electrical impulses are sent through the electrode at regular interval and the heart is paced to beat with the impulses.

Another aspect of the invention provides a method of ablating tissue. A suction assisted ablation device comprising a support surface, having a first and a second face, a plurality of suction elements disposed adjacent the support surface on the first face, at least one needle electrode disposed adjacent the support surface on the first face and at least one suction conduit operatively connected with the suction elements. The first face of the device is placed adjacent an area of tissue. The tissue is penetrated with the needle electrode. Suction is conducted to the suction elements via the suction conduit. The tissue is grasped with the suction; and ablated.

The foregoing, and other, features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims in equivalence thereof.

DETAILED DESCRIPTION OF THE PRESENTLY PREFERRED EMBODIMENTS

Figure 1:
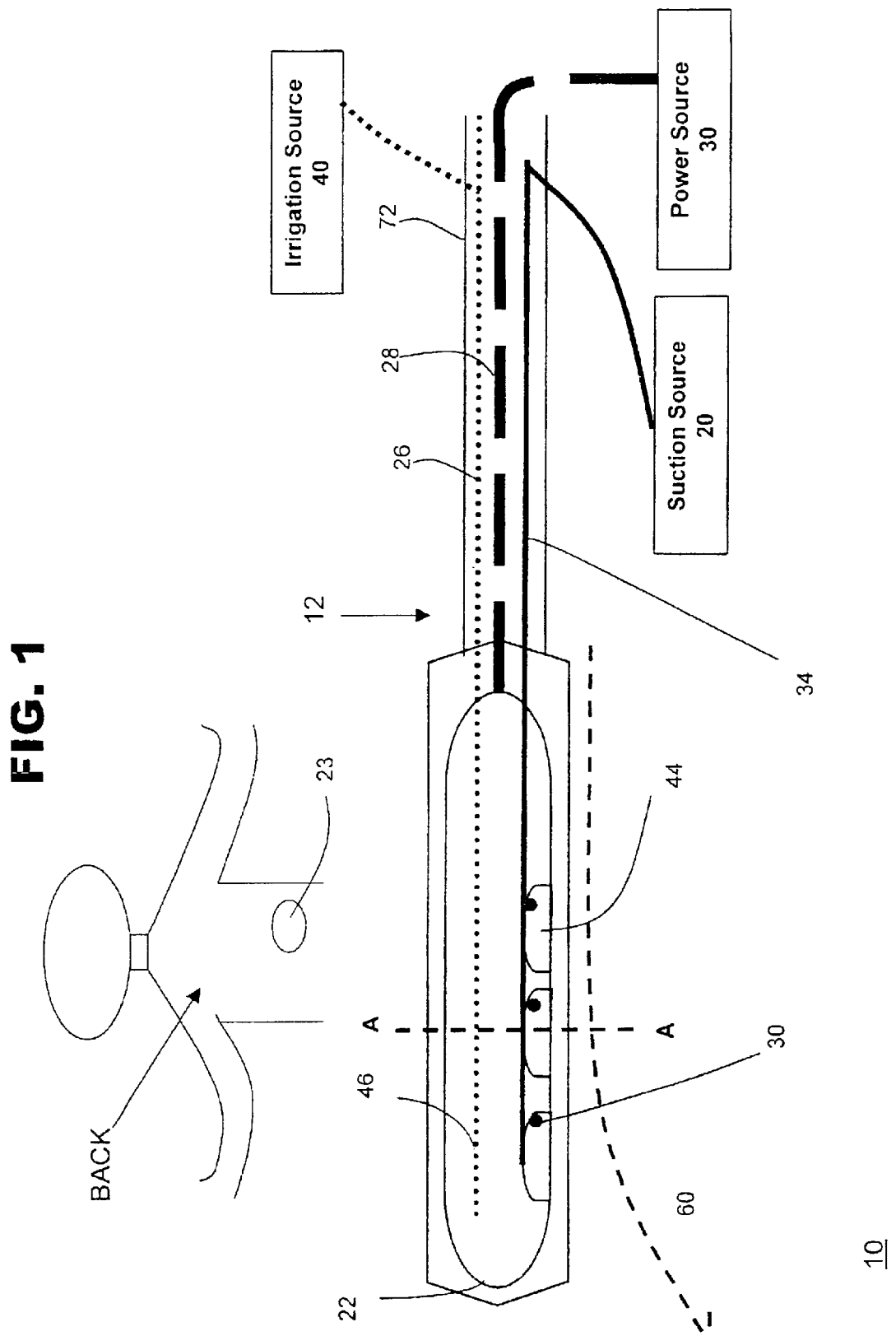
FIG. 1 is a side view of the suction assisted ablation device in accordance with the present invention shown within a system for ablating tissue.

FIG. 1 shows one embodiment of system 10 for ablating tissue, such as organic tissue, in accordance with the present invention. Typically the tissue to be ablated will be located within the body cavity, such as the endocardial or epicardial tissue of the heart. Other body organ tissue, such as the liver, lungs or kidney, may also be ablated using the present invention. Tissue types that may be ablated include skin, muscle or even cancerous tissue or abnormal tissue growth.

System 10 may include an ablation device 12 that comprises at least one conductive element 22, such as an electrode, and a connection 28 to a power source 30. Ablation device 12 may also include one or more suction elements 44 and a suction conduit 34 that provides suction from a suction source 20. System 10 also may include a conduit 26 to an irrigation source 40 that provides irrigation fluid to the ablation site. System 10 may also include temperature-sensitive elements 36, which may have the same power source 30 as the electrodes or may have their own power source.

System 10 may also include an indifferent (non-ablating) electrode 23 which may serve as a return plate for energy transmitted through electrode 22. Electrode 23 may be placed elsewhere on the patient's body other than the ablation site. For example, electrode 23 may be placed on the patient's back, thigh or shoulder.

Ablation device 12 may be any suitable ablation tool such as, for example, a catheter, an electrocautery device, an electrosurgical device, a suction-assisted ablation tool, an ablation pod, an ablation paddle, an ablation hemostat or an ablation wire. Ablation device 12 and its components are preferably made of a biocompatible material such as stainless steel, biocompatible epoxy or biocompatible plastic. Preferably, a biocompatible material prompts little allergenic response from the patient's body and is resistant to corrosion from being placed within the patient's body. Furthermore, the biocompatible material preferably does not cause any additional stress to the patient's body, for example, it does not scrape detrimentally against any elements within the surgical cavity. Alternatively, the biocompatibility of a material may be enhanced by coating the material with a biocompatible coating.

Preferably, ablation device 12 may be permanently or removably attached to a maneuvering apparatus for manipulating device 12 onto a tissue surface. For example, ablation device 12 may be attached to a handle 72 such as shown in FIG. 1. Ablation device 12 may also be located on one or more of the jaws of a hemostat-like device. Ablation device 12 may also be used in conjunction with a traditional catheter, for example, in a closed heart ablation procedure. Ablation device 12 may also be maneuvered with a leash or pull-wire assembly. Ablation device may also be positioned on a pen-like maneuvering apparatus such as the Sprinkler pen available from Medtronic, Inc. Alternatively any appropriate flexible, malleable or rigid handle could be used as a maneuvering apparatus. Alternatively, any appropriate endoscopic or thoroscopic-maneuvering apparatus may also be used with device 12.

Device 12 also preferably includes a connection 28 suitable for conducting energy to device 12, particularly to conductive element 22 from a power source.

The conductive element 22 of ablation device 12 may preferably be an electrode. This electrode 22 may be positioned in any suitable place on device 12. Preferably electrode 22 is placed near an end of the device 12, away from the user, to be more easily manipulated against the tissue 60 to be ablated.

Figure 2:
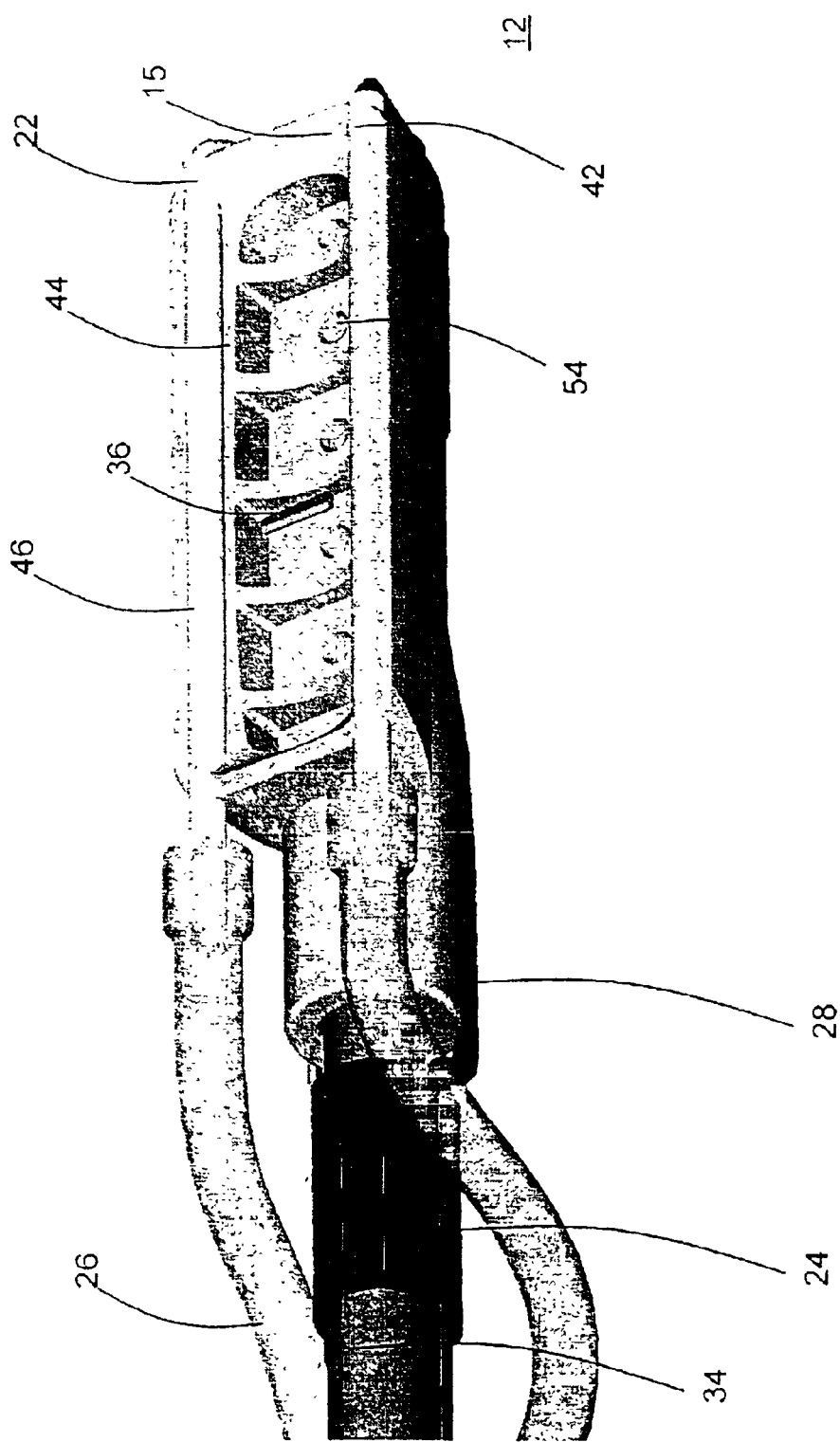
FIG. 2 is a bottom view of one embodiment of the suction assisted ablation device of the present invention, showing a first configuration of the suction elements and of the ablation electrodes.

FIG. 2 shows one embodiment of a device 12 for ablating organic tissue in accordance with system 10 of the present invention. Suction assisted ablation device 12 may comprise at least one face 15 that may conform to the surface of the target tissue 60. The face 15 may be any configuration that conforms to the surface of the target tissue, such as the slightly curved or arcuate configuration of FIG. 1. Suction device 12 may also include a suction conduit 34 that may be connected to least one suction port 44 containing a suction opening 54 Suction device may also have at least one conductive element 22 disposed adjacent face 15. For example, two conductive elements 22, 42 are shown in FIG. 2. Preferably, the conductive element 22, 42 may be an electrode. Alternatively, suction device 12 may be made of a conductive polymer and may serve as a conductive element. The distal end of device 12 may be positioned near the ablation site and the proximal end may be positioned towards the surgeon.

Preferably, when face 15 of suction device 12 is positioned against the target tissue, face 15 is adapted to conform to the surface of the tissue. This may be accomplished by making suction device 12 from a flexible material, such as, for example, a pliable polymer, biocompatible rubber thermoplastic elastomer or PVC. Alternatively, suction device 12 may be made of a more rigid material covered with an elastic over face 15. Suction force being applied through device 12 may cause device 12 to conform more closely to the shape of the target tissue. Device 12 may also be made of a malleable stainless steel or other material that is shapeable but not necessary flexible. Device 12 may also be made of a conductive polymer.

Ablation device 12 may also be permanently or removably attached to a suction tube 24. Suction conduit 34 may be located within Tube 24. Conduit 34 may communicate suction to the target tissue surface via the suction openings 54 of suction ports 44 in device 12.

The suction ports 44 may be arranged three to six ports in a row, although the specific number of ports and their position may vary. Preferably, for a linear lesion to result from the ablation process, the ports are arranged linearly. Device 12 may be covered with a covering during insertion to prevent blood or tissue from clogging the ports 44, although this is not necessary. Such coverings may include coverings of biocompatible material that would cover device 12. Alternatively, coverings may be placed over ports 44, such as, for example, mesh coverings or ribbed coverings.

Each suction port 44 has a suction opening 54, which may be located in the center or at a position slightly off-center of suction port 44. Although the openings 54 are circular in FIG. 2, other shapes may be used The suction ports 44 may also be any suitable shape. For example, in the embodiment of FIG. 2, the ports 44 are rectangular. Additionally, suction openings 54 may be covered with a covering such as described above to prevent blood or tissue from clogging the openings 54.

Preferably, each suction opening 54 has a smaller diameter than the area of suction port 44. This creates a high resistance pathway between suction port 44 and suction conduit 34. Because of this, loss of a tissue-to-port seal in one suction port (and thus loss of fixation of the suction port to the tissue) should not cause a precipitous pressure drop in the remainder of the suction ports.

Ablation device 12 may be permanently or removably attached to at least one connection 28 for conveying energy to electrodes 22, 42 from power source 30. This energy is typically electrical, such as radiofrequency (RF) energy. However, it may also be any appropriate type of energy such as, for example, microwave or ultrasound energy. Preferably, electrode 22 runs the length of one side of device 12 and electrode 42 runs the length of the opposite side of device 12. Electrode 22 may be maneuvered into contact with the target tissue to ablate the tissue. In the embodiment of FIG. 2, two electrodes are shown in a bipolar arrangement. In such a bipolar arrangement, electrode 42 may also be maneuvered into contact with target tissue 60 to ablate the tissue.

Ablation device 12 may be permanently or removably attached to at least one fluid conduit 26 for irrigating the ablation site with a fluid. Alternatively, ablation site may not be irrigated. Fluid is conveyed to the site via fluid openings 46 which are preferably integrated into electrodes 22, 42. However, fluid may be delivered to the site via a separate irrigation mechanism, such as an irrigation pump (not shown). Moreover, fluid openings 46 may be disposed in any appropriate manner on device 12.

Suction ablation device 12 may be colored so that it can be easily visible against the target tissue. Alternatively, it may be clear to provide less distraction to the surgeon or to provide viewing of blood or other material being suctioned. Suction tube 24 may be a flexible tube constructed of a soft plastic which could be clear or colored. Suction ports 44 may be constructed of biocompatible rubber or epoxy, which could be clear or colored.

Electrodes 22, 42 may be constructed of stainless steel, platinum, other alloys, or a conductive polymer. If device 12 is made of a more flexible material, electrodes 22, 42 may be made of materials that would flex with the device 12. Such flexible electrodes may be, for example, made in a coil or spring configuration. Flexible electrodes 22, 42 may also be made from a gel, such as a hydrogel. Furthermore, electrodes 22, 42 may also be an electrode designed to deliver fluid, such as, for example, a microporous electrode, a "weeping" electrode, or an electrode made of a hydrogel.

A source 20 for creating suction may be attached to suction tube 24 at the proximal end, preferably by a standard connector. This suction source 20 may be the standard suction available in the operating room and may be coupled to the device 12 with a buffer flask (not shown). Suction is provided at a negative pressure of between 200-600 mm Hg with 400 mm Hg preferred.

System 10 may include at least one temperature-sensitive element 36. The temperature-sensitive element 36 is positioned to communicate with at least one of suction ports 44. Preferably, an element 36 is positioned to communicate with each suction port 44. These elements may be, for example, thermocouple wires, thermisters or thermochromatic inks. These thermocouple elements allow temperature to be measured. Such monitoring of temperature may crucial. Too high a temperature will char the tissue or cause the blood at the ablation site to coagulate. Preferably, the elements 36 may be adhered within suction ports 44 so as to contact the tissue when it is suctioned into the ports. Thermocouple elements that may be used are 30 gauge type T thermocouple wire from Dodge Phelps Company. One type of conductive epoxy which may be used to adhere the elements is epoxy no. BA-2902, available from Trecon.

A separate temperature sensitive element 36 may be adhered or mounted within each suction port 44. Alternatively, a temperature sensitive element may be incorporated to run through all of the suctions ports 44.

As ablation occurs, it is sometimes desirable to irrigate the ablation site with irrigation fluid, which may be, for example, any suitable fluid such as saline, an ionic fluid that is conductive or another conductive fluid. The irrigating fluid may cool the electrode 22 of ablation device 12. Irrigated ablation is also known to create deeper lesions that are more likely to be transmural. Transmurality is achieved when the full thickness of the target tissue is ablated. The application of fluid to an ablation site may also prevent electrodes, particularly metal electrodes, from contacting the target tissue. Direct contact of electrodes to the target tissue may char or burn the tissue, which may clog the device. Furthermore, continuous fluid flow may keep the ablation device surface temperature below the threshold for blood coagulation, which may also clog the device Use of irrigating fluid may therefore reduce the need to remove a clogged ablation device for cleaning or replacement. The presence of an ionic fluid layer between electrode 22 and the tissue to be ablated may also ensure that an ionic fluid layer conforming to the tissue contours is created. In one preferred embodiment, saline solution is used. Alternatively, other energy-conducting liquids, such as Ringer's solution, ionic contrast, or even blood, may be used. Diagnostic or therapeutic agents, such as Lidocaine, $CA^{++}$ blockers, or gene therapy agents may also be delivered before, with or after the delivery of the irrigating fluid. Irrigation source 40 may be any suitable source of irrigation fluid such as, for example, a standard irrigation pump (not shown). This pump may also be connected to power source 30 or may have its own source of power. Preferably, device 12 also includes a conduit 26 for delivering irrigation to the ablation site from irrigation source 40.

In the embodiment of FIG. 1, fluid openings 46 may be located within the electrode 22 itself. These openings may be holes machined into the electrode 22. These openings may deliver fluid to the ablation site as described above. Furthermore, electrode 22 may also be an electrode designed to deliver fluid, such as, for example, a microporous electrode, a "weeping" electrode, an electrode made of a microporous polymer or an electrode made of a hydrogel.

Figure 3:
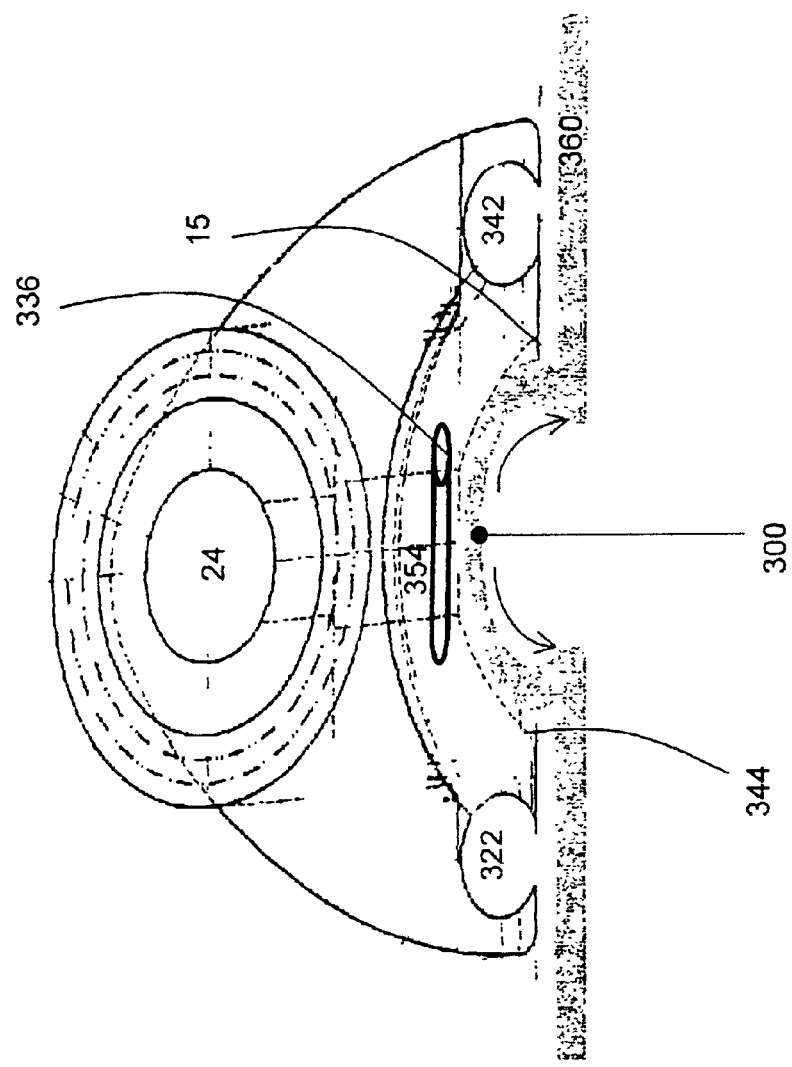
FIG. 3 is a cross-sectional view of one embodiment of the suction assisted ablation device of the present invention, showing suction activity and ablation pattern at one suction site.

Referring now to FIG. 3, a close-up cross section is shown, taken along line A—A of FIG. 1. In use, the embodiment of device 12 shown in FIGS. 1 and 2 is placed against target tissue 360 so that when a suction force is applied through openings 354, the target tissue is pulled into the suction port 344. Fluid flows from openings 46 towards the target tissue as indicated by the arrows. Openings 46 are preferably angled at about 30 degrees. Openings 46 preferably face towards suction ports 344. Ablation may begin at point 300 of the tissue and spread in the direction indicated by the dotted arrows. If left over time, the entire piece of tissue suctioned into the ports 344 may be ablated.

Electrodes 322, 342 are brought to a temperature sufficient to ablate the tissue within the ports 44. Thermocouple elements 336 may be used to monitor the temperature and when a given threshold temperature is reached, the surgeon may end ablation. This configuration of device 12 is especially useful because it gives an accurate measurement of the tissue temperature since the tissue 360 is in direct contact with the thermocouple elements 336 located near ports 344. Thus the temperature of the tissue may be measured by thermocouple elements rather than the temperature of the electrode 322 being measured. The temperature of the tissue may also be determined based on ablation time.

The resulting lesion may be transmural. If the tissue is allowed to heat until the elements 336 indicate a temperature that usually indicates cell death (such as, for example, 15 seconds at 55°), this may indicate that all the tissue has reached this temperature. In turn, this may indicate that the lesion is transmural.

The ablation resulting from the arrangement of electrodes in FIGS. 2 and 3 is linear. The width of the resulting ablation lesion may be determined by the space between electrodes 22, 42. The width of the resulting ablation lesion may also be determined by the depth of the suction port 44 and the amount of the tissue suctioned into port 44 The depth of the lesion may be controlled by the depth of the suction port 44 and the amount of suction force applied. The depth of the lesion may also be determined by the power applied to the conductive element and the length of ablation time. The lesion resulting from the suction port 344 of FIG. 3 will be repeated at each subsequent corresponding suction port along the length of device 12. It is contemplated that for a longer lesion, a longer pod could be used or a series of pods could be strung together. A single pod could also be used to create a longer lesion by ablating to create a first lesion and then being moved to create a second lesion in line with the first lesion.

Figure 4:
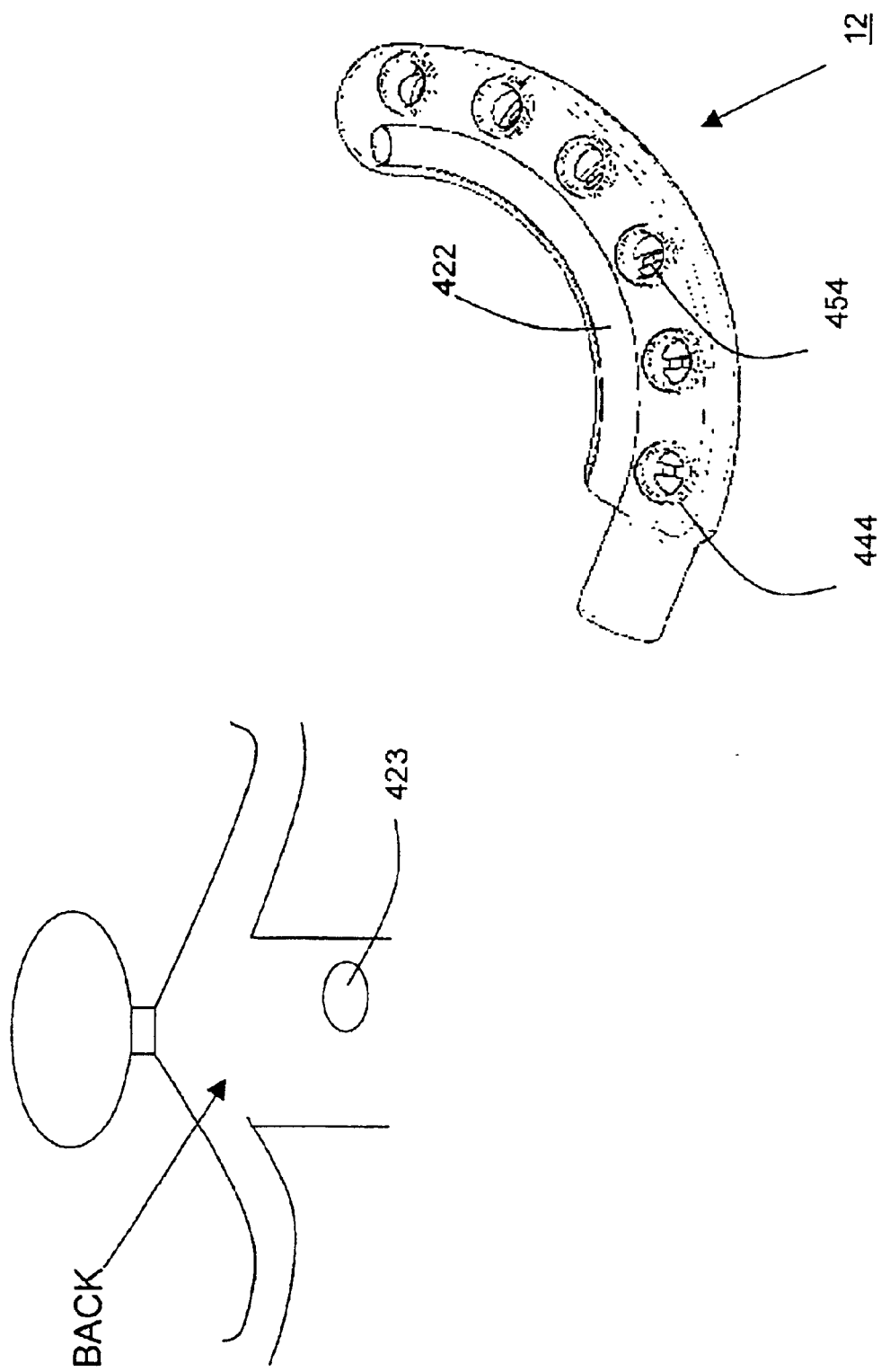
FIG. 4 is a bottom view of a second embodiment of the suction assisted ablation device of the present invention, showing a second configuration of the suction elements and of the ablation electrodes.

FIG. 4 shows another embodiment of the invention shown in FIG. 3. In this embodiment, electrodes 422, 423 are arranged in a unipolar arrangement. Electrode 422 is placed on the device 12 while another electrode 423 acts as a ground patch (indifferent, or non-ablating electrode) and is placed separately from the device 12. For example, electrode 422 on device 12 could be placed on a surface of the heart. Then corresponding electrode 423, which could be on a separate support surface, could be placed on the back of the patient to complete the circuit. Although the suction ports 444 may be arranged in a linear manner, ports 444 may be arranged in any other appropriate configuration, including for example, in an arcuate or radial arrangement. Although suction openings 454 may be circular, they may also be any appropriate shape to deliver suction. The lesions created by this sort of unipolar arrangement tend to be wider than those created by a bipolar arrangement.

In the unipolar arrangement of FIG. 4, suction ports 444 are used to grasp target tissue (not shown) but do not pull the tissue into the ports for ablating. Fluid would flow from openings in the electrode 423 or in device 12 in the same manner as described above. Ablation would occur in a similar manner to that described above although the device 12 remains uniformly on the surface of the target tissue rather than pulling the tissue into the ports for ablation.

Figure 5:
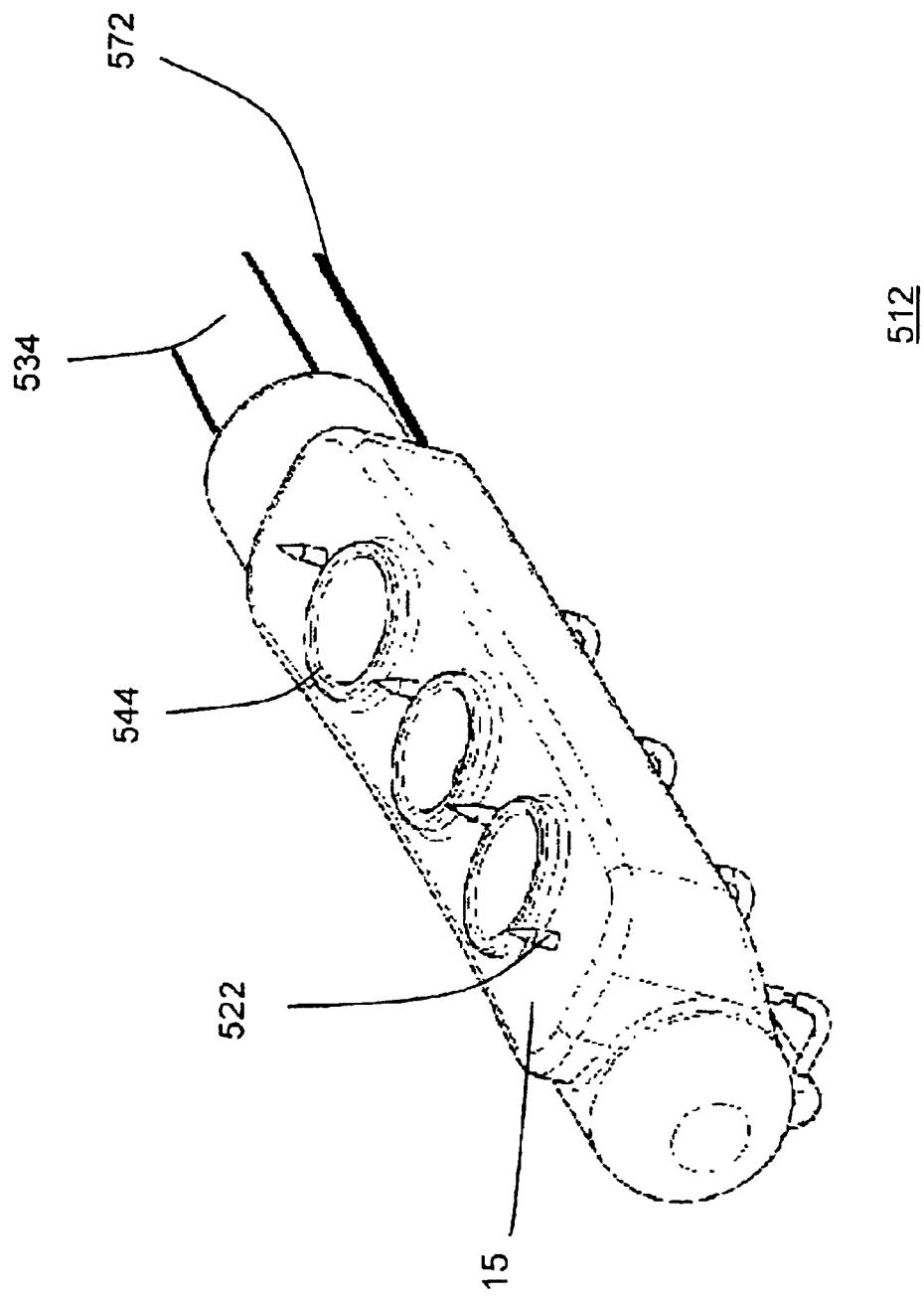
FIG. 5 is a bottom view of another embodiment of the suction assisted ablation device of the present invention.

It is contemplated that the electrodes used in the present invention could include any appropriate electrodes for performing ablation such as, for example, metal electrodes, braided metal electrodes or needle electrodes FIG. 5 shows another embodiment of the suction ablation device 512 of the present invention, in which the conductive element may be a series of needle electrodes 522. A unipolar arrangement of the electrodes 522 is shown. Alternatively, the electrodes may be arranged in a bipolar configuration similar to the arrangement of FIG. 2. In a bipolar arrangement, one series of needle electrodes may be arranged down the length of one side of the suction ports 544 and another series of electrodes 522 arranged down the length of the other side. Needle electrodes may be used to poke through fatty tissue covering the target tissue. They may then be used to poke into the target tissue. Suction may then be applied as described above to hold electrodes in place. Ablation may then occur as described above. Additionally, device 512 shows suction conduit 534 which may provide suction to ports 544 and pull wire 572 that serves as a maneuvering apparatus for device 512.

The device 12 may also be used in electrical mapping functions. For example, electrode 22 may be placed on one area of the heart and an appropriate signal sent through it. Then the electrode 42 may receive the signal from electrode 22. From the strength of the signal, the distance of electrode 22 from electrode 42 may be determined. Conduction delay or block can help determine transmurality of lesions.

Device 12 may also be used in pacing functions. For example, device 12 may grasp the heart as described above. Then energy may be sent through electrodes, 22, 42 at regular intervals. This energy may cause the heart to beat simultaneously to the signals sent through electrodes 22, 42. The device 12 may thus pace the heart at an appropriate beating rate, thereby serving as a pacemaker. This may be used, for example, during a surgical procedure when it might be necessary to regulate the heart's beating temporarily.

It should be appreciated that the embodiments described above are to be considered in all respects only illustrative and not restrictive. The scope of the invention is indicated by the following claims rather than by the foregoing description. All changes that come within the meaning and range of equivalents are to be embraced within their scope.

We claim:

1. A suction assisted ablation device comprising:
    a support surface;
    at least three suction ports disposed adjacent the support surface, each of said at least three suction ports positioned adjacent the support surface in a substantially linear arrangement with respect to each other; and
    a plurality of needle electrodes disposed adjacent the support surface and extending adjacent the suction ports, the plurality of needle electrodes disposed such that a linear transmural lesion may be formed in tissue by applying radio frequency energy to the tissue via the plurality of electrodes.

2. The device of claim 1 further comprising:
    a maneuvering apparatus operatively connected with the support surface.

3. The device of claim 2 wherein the maneuvering apparatus comprises at least one pull wire.

4. The device of claim 1 further comprising:
    at least one thermocouple element adjacent the suction elements.

5. The device of claim 1 wherein the needle electrodes are arranged with a first series of the needle electrodes along a first side of the suction ports and a second series of the electrodes arranged along a second side of the suction ports.

6. The device of claim 1 wherein at least some of the needle electrodes are centered between the suction ports.

7. The device of claim 1 further comprising:
    at least one fluid opening disposed adjacent the support surface.

8. A suction assisted ablation device comprising:
    a support surface;
    at least three Suction ports disposed adjacent the support surface, each of said at least three suction ports positioned adjacent the support surface in a substantially linear arrangement with respect to each other;
    a plurality of conductive elements disposed adjacent the support surface and extending adjacent the suction ports, at least a portion of the conductive elements having a fluid opening therein; the plurality of conductive elements disposed such that a linear transmural lesion may be formed in tissue by applying radio frequency energy to the tissue via the plurality of conductive elements.

9. The device of claim 8 further comprising:
    a maneuvering apparatus operatively connected with the support surface.

10. The device of claim 9 wherein the maneuvering apparatus comprises at least one pull wire.

11. The device of claim 9 further comprising:
    at least one thermocouple element adjacent the suction elements.

12. The device of claim 9 wherein the conductive elements are arranged with a first portion of the conductive elements along a first side of the suction ports and a second portion of the conductive elements arranged along a second side of the suction ports.

13. The device of claim 9 wherein at least some of the conductive elements are centered between the suction ports.

14. A method of ablating tissue comprising:
    providing a suction assisted ablation device comprising a support surface, a plurality of suction elements disposed adjacent the support surface, a plurality of needle electrodes disposed adjacent the support surface and at least one suction conduit operatively connected with the suction elements;
    placing the device adjacent an area of tissue;
    penetrating the tissue with the needle electrode;
    conducting suction to the suction elements via the suction conduit;
    grasping the tissue with the suction; and
    applying radio frequency energy to the tissue via the plurality of electrodes such that a linear transmural lesion is formed in the tissue grasped with the suction.

15. The method of claim 14 wherein the device is placed by manipulating an apparatus operatively connected to the support surface.

16. The method of claim 15 wherein the device is manipulated by activating at least one pull wire.

17. The method of claim 15 wherein the device is manipulated by moving a handle.

18. The method of claim 15 wherein the device is manipulated by a catheter.

19. The method of claim 14 further comprising:
    stopping the ablation of the tissue when the temperature monitored by a temperature sensing element adjacent the suction element reaches a given level.

20. A method of treating tissue comprising:
providing a suction assisted device comprising a support surface, a plurality of suction elements disposed adjacent the support surface, and a plurality of conductive element disposed adjacent the support surface, at least some of the conductive elements having a fluid opening;
placing the support surface adjacent an area of tissue;
conducting suction to the suction element;
grasping the tissue with the suction;
penetrating the tissue with the conductive elements;
releasing fluid via the fluid opening; and
ablating the tissue.

21. The method of claim 20 wherein the fluid is an energy-conducting fluid.

22. The method of claim 20 wherein the device is placed by manipulating an apparatus operatively connected to the support surface.

23. The method of claim 20 wherein the device is manipulated by activating at least one pull wire.

24. The method of claim 23 wherein the device is manipulated by moving a handle.

25. The method of claim 23 wherein the device is manipulated by a catheter.

26. The method of claim 23 wherein the conductive element is a needle.

27. The method of claim 20 further comprising monitoring temperature with a temperature-sensitive element in communication with at least one suction element.

28. The method of claim 27 further comprising discontinuing the ablation of tissue when the temperature being monitored reaches a given level.

* * * * *